United States Patent
Smartt et al.

(10) Patent No.: US 11,084,978 B2
(45) Date of Patent: *Aug. 10, 2021

(54) FLUORESCENT COMPOSITIONS

(71) Applicant: National Technology & Engineering Solutions of Sandia, LLC, Albuquerque, NM (US)

(72) Inventors: Heidi A. Smartt, Albuquerque, NM (US); Dianna S. Blair, Albuquerque, NM (US); Juan A. Romero, Bayfield, CO (US); Patrick L. Feng, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/741,843

(22) Filed: Jan. 14, 2020

(65) Prior Publication Data
US 2020/0148946 A1 May 14, 2020

Related U.S. Application Data

(62) Division of application No. 15/898,906, filed on Feb. 19, 2018, now Pat. No. 10,538,701.

(51) Int. Cl.
| | |
|---|---|
| *C09K 11/07* | (2006.01) |
| *C09K 11/54* | (2006.01) |
| *C09K 11/58* | (2006.01) |
| *C09K 11/60* | (2006.01) |
| *C09D 5/22* | (2006.01) |
| *B33Y 80/00* | (2015.01) |
| *B33Y 10/00* | (2015.01) |
| *C09B 15/00* | (2006.01) |
| *C09B 57/02* | (2006.01) |
| *C09B 6/00* | (2006.01) |
| *C07D 311/82* | (2006.01) |
| *C09B 57/14* | (2006.01) |

(52) U.S. Cl.
CPC .............. *C09K 11/07* (2013.01); *C09K 11/54* (2013.01); *C09K 11/58* (2013.01); *C09K 11/60* (2013.01); *B33Y 10/00* (2014.12); *C07D 311/82* (2013.01); *C09B 6/00* (2013.01); *C09B 15/00* (2013.01); *C09B 57/02* (2013.01); *C09B 57/14* (2013.01)

(58) Field of Classification Search
CPC ...................................................... C09K 11/07
See application file for complete search history.

(56) References Cited

U.S. PATENT DOCUMENTS

| | | | |
|---|---|---|---|
| 6,574,945 B2 * | 6/2003 | Martinez, Jr. ............. | B65B 9/02 206/219 |
| 7,959,835 B2 | 6/2011 | Cranor et al. | |
| 2007/0079722 A1 | 4/2007 | Parish | |
| 2008/0157039 A1 * | 7/2008 | Zuckerman ............ | C09K 11/07 252/700 |

OTHER PUBLICATIONS

Odom et al., ACS Appl. Mater. Interfaces 2011, 3, 4547-4551.*

* cited by examiner

Primary Examiner — Vu A Nguyen
(74) Attorney, Agent, or Firm — Daniel J. Jenkins

(57) ABSTRACT

An article that includes a fluorescent composition having at least one of a fluorescent sensor compound and organic reporter molecules encapsulated in a microsphere structure. When encapsulated, the fluorescent sensor compound and the organic reporter molecules are distributed in a liquid organic matrix. When non-encapsulated, the remaining one of the fluorescent sensor compound and the organic reporter molecules reside in the matrix. In response to a force applied to the composition sufficient to break at least a portion of the microsphere structure, the fluorescent sensor compound and the organic reporter molecules are transformed into a non-reversible fluorescent state exhibiting a quantum yield greater than 0.2. The fluorescent state is objectively visually verifiable without physically contacting the composition.

17 Claims, 1 Drawing Sheet

FLUORESCENT COMPOSITIONS

CROSS-REFERENCE TO RELATED APPLICATIONS

This application is a divisional of U.S. patent application Ser. No. 15/898,906, filed on Feb. 19, 2018, entitled "FLUORESCENT COMPOSITIONS," the entirety of which is incorporated herein by reference.

GOVERNMENT INTEREST STATEMENT

The United States Government has rights in this invention pursuant to Contract No. DE-AC04-94AL85000 between the U.S. Department of Energy and Sandia Corporation, and Contract No. DE-NA0003525 between the United States Department of Energy and National Technology & Engineering Solutions of Sandia, LLC, for the operation of the Sandia National Laboratories.

FIELD OF THE INVENTION

The present invention is directed to a fluorescent composition and an article substrate coated by or an article base material combined with the fluorescent composition.

BACKGROUND OF THE INVENTION

It is often desirable to utilize tamper-indicating barriers, such as a tamper-indicating seal that is secured over an opening of a medication container. Ideally, a tamper-indicating barrier would have at least the following attributes: non-repairability (i.e., inability to conceal evidence of tampering), permit quick and reliable objective passive verification of tampering evidence without physical contact with an asset container, permit flexibility as to forming the tamper-indicating barrier (e.g., size, shape, and application), and low cost associated with forming the tamper-indicating barrier.

However, there are considerable challenges associated with creating tamper-indicating barriers for assets or containers of assets, especially for containers of large assets, and no single conventional tamper-indicating barrier can satisfy all the above-mentioned attributes.

SUMMARY OF THE INVENTION

The disclosure is directed to a fluorescent composition including at least one of a fluorescent sensor compound and organic reporter molecules encapsulated in a microsphere structure. When encapsulated, the fluorescent sensor compound and the organic reporter molecules are distributed in a liquid organic matrix. When non-encapsulated, the remaining one of the fluorescent sensor compound and the organic reporter molecules reside in the matrix. In response to a force applied to the composition sufficient to break at least a portion of the microsphere structure, the fluorescent sensor compound and the organic reporter molecules are transformed into a non-reversible fluorescent state exhibiting a quantum yield greater than 0.2. The fluorescent state is objectively visually verifiable without physically contacting the composition.

The disclosure is also directed to an article including a substrate and a coating including the composition of claim 1 applied over the substrate.

The disclosure is yet further directed to an article including a base material combined with the composition of claim 1 to form the article.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
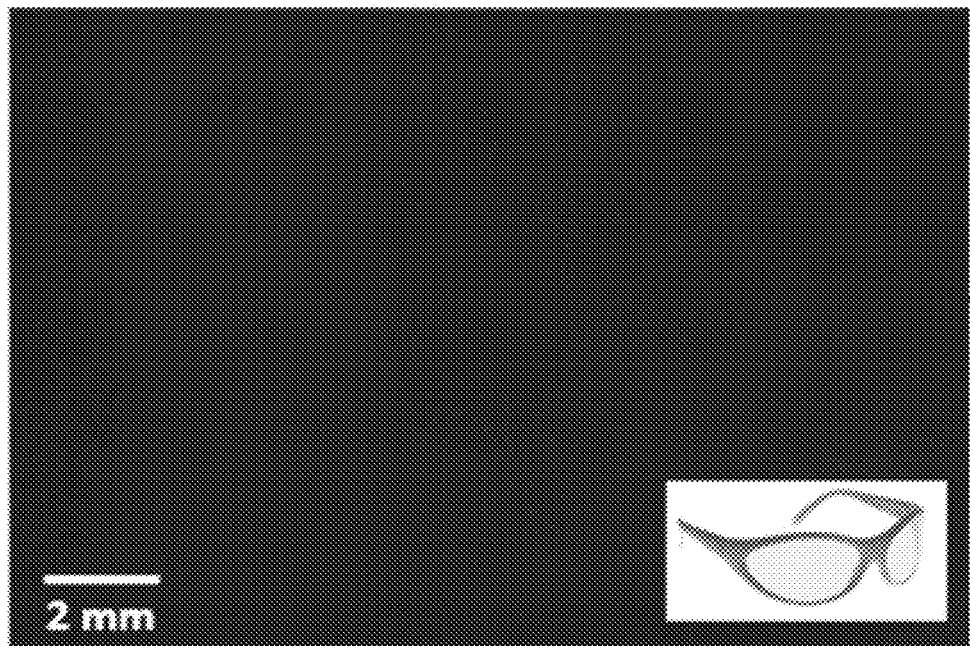
FIG. 1 shows a lack of illumination of an exemplary fluorescent composition with intact microspheres of the present invention when viewed through a long-pass optical filter.

The fluorescent composition of the present invention provides benefits, such as conformal/flexible, scalable, cost-effective tamper-indicating enclosures (TIEs) with obvious and robust responses to tamper attempts, as well as the tamper-indicating barrier or seal applied over the surface of an asset. This tamper-indicating barrier operates as a 'passive' detector in that it is deployed in an unmonitored/unpowered state and is then inspected at subsequent intervals. This invention results in more efficient and effective monitoring as inspectors will require little or no additional equipment, and will be able to immediately detect tampering via simple visual inspection of the fluorescence response. The observation of fluorescence specific to the selected TIE analyte provides a sensitive and robust detection method due to the intrinsically low or non-existent background fluorescence at the specific TIE emission wavelengths. Applications can include custom TIEs (cabinets or equipment enclosures), spray-coating of walls or structures containing or at least partially surrounding an asset, spray-coatings of assets, such as circuit boards, and 3D printed or molded seal bodies.

For purposes herein, the terms "tamper-indicating enclosures" "TIEs" and the like are not only intended to include articles, such as containers, including walls and structures that surroundingly encase/isolate/protect valuable assets, but to also include the valuable assets (e.g., a circuit board) themselves.

For purposes herein, the term "article" and the like is also intended to include the valuable assets (e.g., a circuit board) themselves.

For purposes herein, the terms "fluorescent sensor compound," "fluorophore," "turn-on fluorophore," "turn-on fluorescent molecules" and the like may be used interchangeably.

For purposes herein, the terms "microcapsules," "microsphere," "microspheres," "microsphere structure" and the like may be used interchangeably.

For purposes herein, the term "objectively visually verifiable" is intended to mean that with minimal equipment, such as an excitation source, such as a UV excitation source used by itself as viewed without further enhancement by an inspector having visual acuity considered acceptable for performing such inspections. Alternately the term "objectively visually verifiable" is intended to include the excitation source in combination with a visual aid provided to the inspector, at least one of an indication of tampering or an indication of a lack of tampering is visually present, wherein such indications are essentially mutually exclusive of each other, and cannot occur simultaneously.

In a composition of the present invention, fluorescent sensor compounds are utilized as a turn-on fluorescent mechanism for TIEs. More specifically, fluorescent sensor compounds are encapsulated in microspheres, such as copolymer or silica microspheres in a matrix such as a liquid organic matrix containing organic reporter molecules. The purpose of the reporter molecules is to induce a permanent fluorescence change in the sensor compounds upon contact of these two components. In response to the rupture of at least a portion of the microspheres in response to a force applied to the microspheres of the composition, the force acting over a predetermined area of the microspheres, a mixing/mass transfer of the fluorescent sensor compounds and organic reporter molecules occurs. As a result of this mixing/mass transfer, the fluorescent sensor compounds and organic reporter molecules are transformed from a dark or non-fluorescent state into a non-reversible fluorescent state exhibiting a quantum yield greater than 0.2. In one embodiment, the quantum yield is between 0.7 and 1.0, with 1.0 being the maximum value. The resulting fluorescent state is objectively visually verifiable without physically contacting the composition. This contactless verification process is classified as a nondestructive evaluation method.

In one embodiment, the organic reporter molecules may also be encapsulated in the microsphere structure separately from the encapsulated fluorescent sensor compound. In one embodiment only, the organic reporter molecules may be encapsulated in the microsphere structure, while the fluorescent sensor compound resides in the matrix. In one embodiment, only the fluorescent sensor compound may be encapsulated in the microsphere structure, while the organic reporter molecules reside in the matrix. In each of these embodiments, upon rupture of the microsphere structure(s), mixing/mass transfer of the fluorescent sensor compound in the organic reporter molecules occurs further resulting in the transformation from the non-fluorescent state to a non-reversible fluorescent state.

The turn-on fluorescence response may be accomplished for organic reporter molecules according to different strategies that comprise: (1) an ion-induced conformational change, (2) a change in pH, (3) a Förster Resonance Energy Transfer (FRET), and/or (4) charge-transfer complex or exciplex formation. All of these methods require mixing/mass transport between the fluorophore and the organic reporter molecules that induces the fluorescence change. This may be achieved by configuring the system such that the fluorophore is microencapsulated and the organic reporter molecules reside in the bulk matrix, or vice versa. Alternatively, both the fluorophore and the organic reporter molecules may be microencapsulated separately and then distributed within the surrounding matrix.

Listed below are considerations related to the selection of turn-on fluorophore:

1) Ion-induced conformation change. There are numerous known turn-on fluorescent molecules that operate on the basis of conformational change upon interaction with different ions. One category involves the binding of a metal ion such as $Fe^{3+}$, $Cu^{2+}$, or $Zn^{2+}$ to oxygen and/or nitrogen atoms on the fluorophore, such as by chelation, which leads to a conversion from a dark or non-fluorescent state or non-luminescent conformation to a fluorescent state exhibiting a high quantum yield (as discussed above) or highly fluorescent conformation. In another embodiment, the fluorophore may be responsive to surfactants such as sodium dodecylsulfate. Examples of the above turn-on fluorescent sensors include compounds based upon spirolactam, rhodamine, coumarin, acridine, phenanthrene, eosin, quinoline, and anthracene fluorophores, among others. In one embodiment, a rhodamine spirolactam compound that has $\phi f$, intrinsic=<0.01 and $\phi f, Fe^{3+}$=0.97, where $\phi f$, intrinsic represents the fluorescence quantum yield of the rhodamine spirolactam compound, whereas $\phi f, Fe^{3+}$ represents the fluorescence quantum yield of the rhodamine spirolactam compound after binding to an $Fe^{3+}$ ion.

2) Change in pH. The sensor may also comprise an organic fluorophore that exhibits turn-on fluorescence as a function of a change of or varying pH. Representative examples of such compounds include coumarins, imadozopyridinium compounds, carboxynaphthofluorescein, aminoacridine hydrochloride, ammonium naphthalenesulfonic acid, hydroxyl quinolones, sodium pyrenesulfonic acids, and Rhodamine esters, or a combination thereof. These compounds may exhibit true turn-on fluorescence or a solvatochromic shift in the emission spectrum upon exposure to varying pH environments. In the latter case, the detection system may be configured with a band-pass filter to exclude the unperturbed sensor fluorescence while enabling visual detection of tamper.

3) FRET. An extension of the band-pass detection concept described above is the use of FRET as fluorescence detection method. In one embodiment, a short-wavelength emitting fluorescent dye ('donor') is microencapsulated in a polymer or silica shell, with an acceptor fluorophore residing in the surrounding matrix or in separate microcapsules. A long-pass filter in conjunction with a UV excitation source is then used to exclude the intrinsic donor fluorescence while allowing visualization of the acceptor fluorescence that only becomes evident after tamper. An important requirement for this strategy is that the acceptor compound does not exhibit appreciable absorption at the excitation wavelength used to excite the donor compound. Representative examples of potential donor/acceptor FRET pairs include: biphenyl/pyrene, 2,5-diphenyloxazole/rhodamine 6G, and naphthalene/coumarin 540A.

Figure 2:
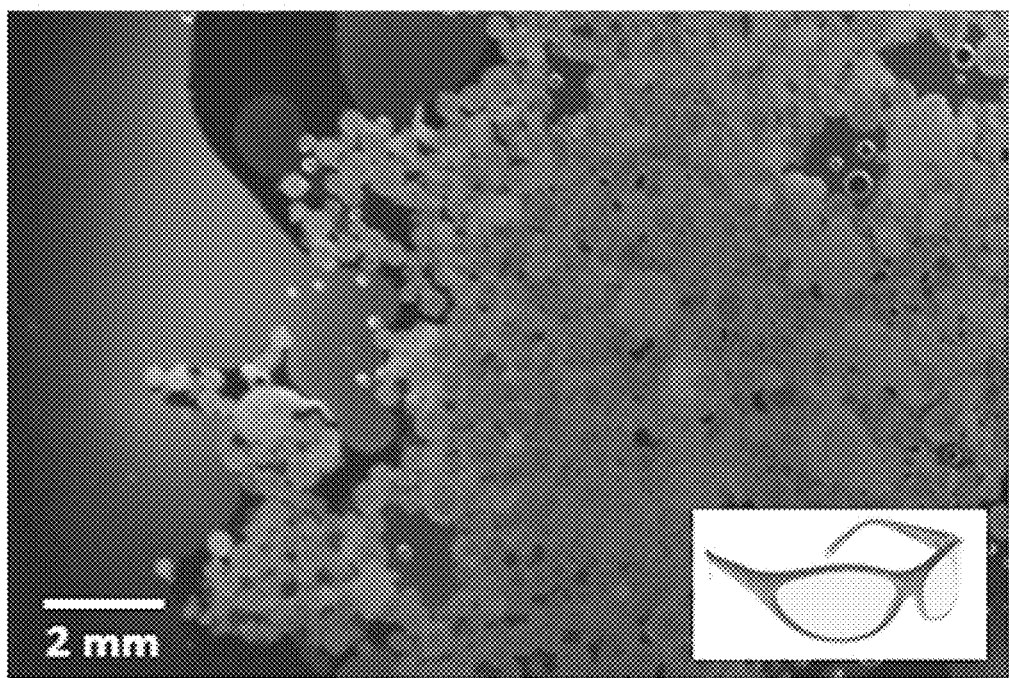
FIG. 2 shows an illumination of an exemplary fluorescent composition with ruptured microspheres of the present invention when viewed through the long-pass optical filter of FIG. 1.

4) Charge-transfer compound or exciplex formation. Charge-transfer fluorescence may also be used to turn on or shift the fluorescence of a microencapsulated tamper-indicating system. An example of such a system is the charge-transfer compound or exciplex formed between anthracene and N,N-diethylaniline, which exhibits a 60 nm red-shift in the emission spectrum following mixing. Other examples include fluorescent charge-transfer species that form between the sensor compound and molecules that contain an amine or nitro group. FIGS. 1 and 2 show the results of a urea-formamide or PMMA microspheres containing an exemplary exiplex-based fluorophore. Pressure-induced breakage (i.e., rupture in response to an application of sufficient pressure to the compound) of the microspheres is visualized by the presence of green luminescence (i.e., would appear green if rendered in color) when viewed through an optical filter, such as a long-pass optical filter (FIG. 2). An example of such a filter is the yellow-tinted sunglasses shown in the inset of FIG. 2. No luminescence is evident in the undamaged fluorescent composition (i.e., intact or unruptured microspheres) when viewed through the same filter (FIG. 1). Stated another way, an optical filter may be used to selectively image the fluorescence response or fluorescent state of interest. That is, the term "selectively image" means that essentially, only the fluorescence response or fluorescent state of interest is contained or is viewable in the filtered image, while excluding any background or 'untampered' fluorescence. This selective imaging is of particular relevance to sensor/analyte combinations based on FRET and charge-transfer fluorescence.

In one embodiment an article comprises a substrate and a coating comprising a composition applied over the substrate. The composition comprises including at least one of a fluorescent sensor compound and organic reporter molecules encapsulated in a microsphere structure. When encapsulated, the fluorescent sensor compound and the organic reporter molecules are distributed in a liquid organic matrix. When non-encapsulated, the remaining one of the fluorescent sensor compound and the organic reporter molecules reside in the matrix. In response to a force applied to the composition sufficient to break at least a portion of the microsphere structure, the fluorescent sensor compound and the organic reporter molecules are transformed into a non-reversible fluorescent state exhibiting a quantum yield greater than 0.2. The fluorescent state is objectively visually verifiable without physically contacting the composition.

In one embodiment, an article comprises a base material combined with a composition to form the article. The composition comprises including at least one of a fluorescent sensor compound and organic reporter molecules encapsulated in a microsphere structure. When encapsulated, the fluorescent sensor compound and the organic reporter molecules are distributed in a liquid organic matrix. When non-encapsulated, the remaining one of the fluorescent sensor compound and the organic reporter molecules reside in the matrix. In response to a force applied to the composition sufficient to break at least a portion of the microsphere structure, the fluorescent sensor compound and the organic reporter molecules are transformed into a non-reversible fluorescent state exhibiting a quantum yield greater than 0.2. The fluorescent state is objectively visually verifiable without physically contacting the composition.

In one embodiment, the fluorescent composite may be configured to achieve different emission spectra following mixing of fluorophores and organic reporter molecules, such as for purposes of ease of visual verification or for other reasons.

In one embodiment, an article may include a layer of the fluorescent composition applied over an exterior surface or substrate of the article. In one embodiment, the fluorescent composition may include a liquid based matrix, permitting application of a layer of the composition over an article substrate such as by brushing or spray painting over the article substrate.

In one embodiment, the fluorescent composition may be incorporated into a base material of a container prior to formation of the container.

In one embodiment, the fluorescent composition may be a fluorophore based on ion/metal-induced fluorescence dissolved in an epoxy matrix, encapsulated by a urea-formamide polymer shell, and dispersed in a 3D printing polymer, such as a thermoplastic or a UV-curable resin. Stated another way, the 3D printing polymer is the base material for forming an article in a layer-by layer manner, such as by a binder jet additive manufacturing technique. That is, the composition is incorporated into a base material of a container prior to formation of the container.

In one embodiment, the fluorescent composition may be a fluorophore based on ion/metal-induced fluorescence dissolved in an epoxy matrix, encapsulated by a urea-formamide polymer shell, and dispersed in a polymer, such as a thermoplastic or resin. Stated another way, the polymer is the base material for forming an article such as by casting or molding. That is, the composition is incorporated into a base material of a container prior to formation of the container.

In one embodiment, the fluorescent composition may be tailored to confer the appropriate microcapsule mechanical properties via intrinsic polymer properties and cross-linking density. For example, emulsion viscosity, shear mixing conditions, and polymerization temperature may be modified to control the particle sizes and wall thicknesses of the microspheres. Modification of these parameters may similarly modify the mechanical sensitivity of tamper indication across a wide range.

Additional information for fluorophores may be collected/recorded/compared, such as the intensity of turn-on fluorescence, susceptibility towards false-positives, and stability under different environmental conditions (thermal, humidity, temporal, ionizing radiation, etc.).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A article comprising:
   a substrate; and
   a material combined with the substrate, the material comprising:
      at least one of a fluorescent sensor compound and organic reporter molecules encapsulated in a microsphere structure;
      wherein the microsphere structure is distributed in a liquid organic matrix;
      wherein when non-encapsulated, the remaining one of the fluorescent sensor compound and the organic reporter molecules reside in the matrix;
      wherein in response to a force applied to the composition sufficient to break at least a portion of the microsphere structure, the fluorescent sensor compound and the organic reporter molecules are transformed into a non-reversible fluorescent state exhibiting a quantum yield greater than 0.2;
      wherein the fluorescent state is objectively visually verifiable without physically contacting the composition.

2. The article of claim 1, wherein the substrate and material are combined by coating the material onto the substrate.

3. The article of claim 1, wherein the article is formed by an additive manufacturing technique.

4. The article of claim 1, wherein the substrate is an exterior surface of a container.

5. The article of claim 1, wherein the substrate and the material are combined by incorporating the material into a base material of a container prior to formation of the container.

6. The article of claim 5, wherein incorporating the material into the base material is achieved by the method selected from a group consisting of at least one of 3-D printing, casting, molding, spraying, or a combination thereof.

7. The article of claim 1, wherein the fluorescence state is achieved as a result of a turn-on fluorescence response accomplished with the fluorescent sensor mixing or in mass transport with the organic reporter molecules contained in the liquid organic matrix, and wherein the turn-on fluorescence is an ion-induced conformational change strategy comprising binding of a metal ion of the reporter to at least one of oxygen and nitrogen atoms of the fluorescent sensor compound.

8. The article of claim 7, wherein the metal ion includes at least one of $Fe^{3+}$, $Cu^{2+}$, and $Zn^{2+}$.

9. The article of claim 1, wherein the fluorescent sensor compound is selected from the group consisting of fluorophores based on spirolactam, rhodamine, coumarin, acridine, phenanthrene, eosin, quinoline, anthracene groups, and combinations thereof.

10. The article of claim 1, wherein the fluorescence state is achieved as a result of a turn-on fluorescence response accomplished with the fluorescent sensor mixing or in mass transport with the organic reporter molecules contained in the liquid organic matrix; and wherein the turn-on fluorescence is a charge-transfer complex formation strategy achieved by the fluorescent sensor compound being responsive to electron-donating or electron-withdrawing components.

11. The article of claim 10, wherein the turn-on fluorescence response is the charge transfer complex formation that comprises electron-donating or electron-withdrawing components selected from the group consisting of amines and nitro-groups.

12. The article of claim 1, wherein the fluorescence state is achieved as a result of a turn-on fluorescence response accomplished with the fluorescent sensor mixing or in mass transport with the organic reporter molecules contained in the liquid organic matrix; and wherein the turn-on fluorescence is an ion-induced conformational change involving the fluorescent sensor compound being responsive to a surfactant of the organic reporter molecules.

13. The article of claim 12, wherein the surfactant is sodium dodecylsulfate.

14. The article of claim 1, wherein the fluorescence state is achieved as a result of a turn-on fluorescence response accomplished with the fluorescent sensor mixing or in mass transport with the organic reporter molecules contained in the liquid organic matrix, wherein the turn-on fluorescence is a change in pH, and wherein, the change in pH strategy includes organic reporter molecules selected from the group consisting of coumarins, imadozopyridinium compounds, carboxynaphthofluorescein, aminoacridine hydrochloride, ammonium naphthalenesulfonic acid, hydroxyl quinolones, sodium pyrenesulfonic acids, rhodamine esters, and combinations thereof.

15. The article of claim 1, wherein the fluorescent sensor compound is a short-wavelength emitting fluorescent donor microencapsulated in a polymer or silica shell and the reporter compound is an acceptor fluorophore residing in the liquid organic matrix or in separate microcapsules.

16. The article of claim 15, wherein pairs of microencapsulated fluorescent donors/acceptor fluorophores are selected from the group consisting of biphenyl/pyrene, 2,5-diphenyloxazole/rhodamine 6G, and naphthalene/coumarin 540A.

17. The article of claim 10, wherein the charge transfer compound formation strategy includes a charge transfer complex formed between anthracene and N,N-diethylaniline that exhibits a red-shift in the emission spectrum following mixing.

* * * * *